US008603946B2

(12) United States Patent
Bernaert et al.

(10) Patent No.: US 8,603,946 B2
(45) Date of Patent: Dec. 10, 2013

(54) PROCESS FOR PRODUCING A BEVERAGE COMPRISING COCOA MATERIAL WITH ENHANCED POLYPHENOL LEVELS

(75) Inventors: Herwig Bernaert, Lebbeke-Wieze (BE); Dirk de Clercq, Lebbeke-Wieze (BE)

(73) Assignee: Barry Callebaut AG, Zurich (CH)

(*) Notice: Subject to any disclaimer, the term of this patent is extended or adjusted under 35 U.S.C. 154(b) by 488 days.

(21) Appl. No.: 12/809,414

(22) PCT Filed: Dec. 19, 2008

(86) PCT No.: PCT/EP2008/010962
§ 371 (c)(1),
(2), (4) Date: Jun. 18, 2010

(87) PCT Pub. No.: WO2009/077206
PCT Pub. Date: Jun. 25, 2009

(65) Prior Publication Data
US 2010/0303924 A1 Dec. 2, 2010

(30) Foreign Application Priority Data
Dec. 19, 2007 (GB) .................................... 0724716.6

(51) Int. Cl.
*A01N 59/00* (2006.01)
(52) U.S. Cl.
USPC .......................................... 504/163; 504/362
(58) Field of Classification Search
USPC ....................................................... 504/163
See application file for complete search history.

(56) References Cited

U.S. PATENT DOCUMENTS

| | | | |
|---|---|---|---|
| 2,117,682 A * | 5/1938 | Sanna ........................ | 426/584 |
| 2,380,158 A | 10/1942 | Burrenmatt et al. | |
| 2,687,959 A | 8/1954 | Siehrs | |
| 2,954,293 A | 9/1960 | Rusoff | |
| 2,977,231 A | 3/1961 | Fox et al. | |
| 3,615,659 A | 10/1971 | Weber | |
| 3,784,715 A | 1/1974 | Arden | |
| 3,982,042 A | 9/1976 | Arden | |
| 4,497,841 A | 2/1985 | Wudel et al. | |
| 4,511,591 A * | 4/1985 | Andersson ................. | 426/603 |
| 4,704,292 A | 11/1987 | Kattenberg | |
| 4,776,173 A | 10/1988 | Kamaei et al. | |
| 4,784,866 A | 11/1988 | Wissgott | |
| 4,871,562 A | 10/1989 | Terauchi et al. | |
| 5,338,554 A | 8/1994 | Vogt et al. | |
| 6,514,555 B1 | 2/2003 | Fayard et al. | |
| 6,517,841 B2 | 2/2003 | Romanczyk et al. | |
| 6,790,966 B2 | 9/2004 | Romanczyk et al. | |
| 7,340,990 B2 | 3/2008 | Halliday et al. | |
| 7,368,144 B2 | 5/2008 | Lecoupeau et al. | |
| 7,919,135 B2 | 4/2011 | Nair et al. | |
| 2002/0061355 A1 | 5/2002 | Martin et al. | |
| 2004/0005347 A1 | 1/2004 | Ter Laak et al. | |
| 2004/0096566 A1 | 5/2004 | Lecoupeau et al. | |
| 2004/0202761 A1 | 10/2004 | Kochhar et al. | |
| 2005/0074521 A1 | 4/2005 | Bartnick et al. | |
| 2007/0042101 A1 | 2/2007 | Troplin et al. | |
| 2007/0077318 A1 | 4/2007 | Pons-Andreu et al. | |
| 2007/0258920 A1 | 11/2007 | Lecoupeau et al. | |
| 2008/0038409 A1 | 2/2008 | Nair et al. | |
| 2008/0193629 A1 | 8/2008 | Pons-Andreu et al. | |
| 2009/0263556 A1 | 10/2009 | Blondeel et al. | |
| 2010/0062138 A1 | 3/2010 | Cienfuegos-Jovellanos Fernandez et al. | |
| 2010/0130422 A1 | 5/2010 | Bernaert et al. | |
| 2010/0184666 A1 | 7/2010 | Bernaert et al. | |
| 2010/0189829 A1 | 7/2010 | Bernaert et al. | |
| 2011/0293789 A1 | 12/2011 | Blondeel et al. | |
| 2012/0003355 A1 | 1/2012 | Bernaert et al. | |

FOREIGN PATENT DOCUMENTS

| | | |
|---|---|---|
| CH | 230897 | 2/1944 |
| CH | 679629 | 3/1992 |
| CN | 1483472 | 3/2004 |
| DE | 2342177 | 7/1974 |
| GB | 797147 | 6/1958 |
| GB | 2182538 | 5/1987 |
| WO | WO 96/10404 | 4/1996 |
| WO | WO 97/36497 | 10/1997 |
| WO | WO 98/09533 | 3/1998 |
| WO | WO 99/45788 | 9/1999 |
| WO | WO 01/93690 | 12/2001 |
| WO | WO 2004/096566 | 11/2004 |
| WO | WO 2008/059064 | 5/2008 |
| WO | WO 2009/118418 | 10/2009 |
| WO | WO 2009/133067 | 11/2009 |

OTHER PUBLICATIONS

Boomgaard et al. "Physical stability of chocolate milk", International Journal of Food Science and Technology, 1987, 22:279-291.*
Gu et al. "Procyanidin and catechin contents and antioxidant capacity of cocoa and chocolate products", J. Agric. Food Chem., 2006, 54:4057-4061.*
Lalande "Fouling of a plate heat exchanger used in ultra-high-temperature sterilization of milk", 1984, 51: 1 page title.*
Bonvchi, Investigation of Aromatic Compounds in Roasted Cocoa Powder, Eur. Food Res. Technol. 221:19-29 (2005).
Cacao et Chocolat—Production Utilisation Caracteristiques, Pontillon (ed), pp. 110-113-270-273, and 315; (Dec. 1997).
Feng, P. et al. ,"Health Care Products for Delaying Senility, Comprises Cleaning Spiny Pear, Mashing, Using Juicer and Filtering, Freeze-Drying or Spray-Drying or Vacuum Drying or Microwave Drying Filtrate to Obtain Spiny Pear Powder", (2004), XP002445704, p. 1.
Handbuch der Kakaoerzeugnisse, $2^{nd}$ Ed., Fincke (ed.), Springer-Verlag Berlin/Heidelberg/New York, (1965).

*Primary Examiner* — Bin Shen
(74) *Attorney, Agent, or Firm* — Hoxie & Associates LLC

(57) ABSTRACT

Process for producing a beverage comprising a cocoa material having an enhanced level of polyphenols, the process comprising the steps of: (a) adding a base to an aqueous phase to adjust the pH to between about 6.5 and about 7.5, (b) mixing ingredients into the aqueous phase to give a dispersion, the ingredients including the cocoa material having an enhanced level of polyphenols, (c) performing a thermal treatment on the dispersion, comprising heating the dispersion to over about 85° C. for at least about 5 seconds, and (d) cooling the treated dispersion. A beverage obtainable by the process is also disclosed.

23 Claims, 2 Drawing Sheets

(56) References Cited

OTHER PUBLICATIONS

Miller et al., Impact of Alkalization on the Antioxidant and Flavanol Content of Commercial Cocoa Powders, J. Agric. Food Chem., vol. 56, pp. 8527-8533, (2008).

Mullin, W.J. et al., "The Macronutrient Content of Fractions from Jerusalem Artichoke Tubers (*Helianthus tuberosus*)", Food Chemistry, (1994), vol. 51, No. 3, XP002445702, (Abstract) pp. 1-2.

Scherz, H. et al., Kakaopulver-Cocoa Powder Cacao en pudre, Food Compositions and Nutritional Tables, (Jan. 1, 2000), XP 002475567.

Talcott et al., Red Clover Isoflavonoids as Anthocyanin Color Enhancing Agents in Muscadine Wine and Juice, Food Research International 38 (10)—1205-23 (2005).

WPI Abstract of CN 1483472; XP-002445704 (2004).

\* cited by examiner

PROCESS FOR PRODUCING A BEVERAGE COMPRISING COCOA MATERIAL WITH ENHANCED POLYPHENOL LEVELS

CROSS-REFERENCE TO RELATED APPLICATIONS

This application is a United States National Stage Application under 35 U.S.C. §371 of PCT/EP2008/010962, filed Dec. 19, 2008, which claims the benefit of GB0724716.6, filed Dec. 19, 2007, the contents of each of which are incorporated herein by reference.

BACKGROUND OF THE INVENTION

The present invention relates to the preparation of a beverage and in particular a beverage that comprises a cocoa based material having an enhanced level of polyphenols.

It is known that fresh cocoa beans contains approximately 40% water, 30 to 35% lipids, 4 to 6% polyphenols or polyphenol derivatives, 1.5% xanthines, with the rest being mainly constituted by proteins, starch, cellulose and sugars. Further information on the composition of cocoa beans may be found in the following articles:

Cocoa procyandins: major flavanoids and identification of some minor metabolites by L. J. Porter, Z. Ma and B. G. Chan, published in Phytochemistry vol. 35, No. 5 p 1657-1663, 1991 and Epicatechin content in fermented and unfermented cocoa beans by H. Kim and P. G. Keeney, published in Journal of Food Science-vol. 49 (1984) p 1090-1092.

Cocoa is grown in South America, Africa and elsewhere. When harvested, its fruits or pods are picked, and the beans undergo a pre-treatment which consists of fermenting for five to six days before being dried. During this fermentation, a certain number of biochemical reactions occur, which involve, in particular, the destruction of pathogenic microorganisms, the formation of aroma precursors and a partial degradation of polyphenols following enzymatic oxidation or tanning of proteins. It is considered that 70 to 80% of polyphenols are degraded during traditional fermentation.

Polyphenols are a diverse group of compounds (Ferriera et al., "Diversity of Structure and Function in Oligomeric Flavanoids, Tetrahedron, 48:10, 1743-1803, 1992). They occur widely in a variety of plants, some of which enter into the food chain. Several thousands of molecules with a polyphenol structure have been identified in higher plants, and several hundreds are found in edible plants. These molecules are secondary metabolites of plants and generally involved in defense against external stressors, like ultraviolet radiation or aggression by pathogens (Manach, C., et al., Polyphenols: food sources and bioavailability. Am J Clin Nutr, 2004. 79: p. 727-47).

Polyphenols may be further classified into different groups as a function of the number of aromatic rings and the structural elements that bind these rings together. Distinctions are made between flavonoids, non-flavonoids and phenolic acids (see FIG. 1), with the flavanoids being the largest group with more than 2000 known compounds. FIG. 1 shows the classification hierarchy of polyphenols with epicatechin, catechin and the procyanidins being the predominant class of polyphenols in cocoa.

Cocoa and cocoa-derived products are rich in polyphenols and particularly in flavonoids, a class of compounds that occur in a wide variety of fruits, vegetables, teas and red wines. It is well documented that cocoa and cocoa products, like chocolate, are among the richest sources of polyphenols (Ding, E., et al., Chocolate and prevention of cardiovascular disease: a systemic review. Nutr & Met, 2006, 3:1-12).

In addition, cocoa has been described as being rich in a particular subgroup of flavonoids named flavanols (flavan-3-ols). The flavanols are present as the monomers epicatechin and catechin or as oligomers of epicatechin and/or catechin called procyanidins. The chemical structures of the different flavanols found in cocoa are shown in FIGS. 2 and 3.

FIG. 2 shows the chemical structure of the flavanol monomers in cocoa. FIG. 3 shows the chemical structure of flavanol dimers and oligomers in cocoa.

An increasing body of evidence supports the concept that dietary intake of polyphenols promotes health and attenuates or delays the onset of various diseases, including cardiovascular diseases, cancer, and other chronic diseases.

Flavanols in cocoa and cocoa products exert some beneficial vascular effects (Schroeter, H., et al., Epicatechin mediates beneficial effects of flavanol-rich cocoa on vascular function in humans. PNAS, 2006. 103: p. 1024-1029; Engler, M. B., et al., Flavonoid-rich dark chocolate improves endothelial function and increases plasma epicatechin concentrations in healthy adults. Journal of the American College of Nutrition, 2004. 23(3): p. 197-204).

Flavanols in cocoa and cocoa products reduce the risk for cardiovascular morbidity and mortality (Buijsse, B., et al., Cocoa intake, blood pressure and cardiovasular mortality. The Zutphen Elderly Study. Arch Intern Med, 2006. 166: p. 411-417). Flavanols in cocoa and cocoa products also reduce the risk for cancer (Yamagishi, M., et al., Chemoprevention of lung carcinogenesis by cacao liquor proanthocyanidins in a male rat multi-organ carcinogenesis model. Cancer letters, 2003. 191: p. 49-57). Flavanols in cocoa and cocoa products may contribute to the prevention of neurodegenerative diseases and diabetes mellitus (Bayard, V., et al., Does flavanol intake influence mortality from nitric oxide-dependent processes? Ischemic heart disease, stroke, diabetes mellitus, and cancer in Panama. Int. J. Med. Sci., 2007. 4(1): p. 53-58).

A research group found that long-term ingestion of cocoa flavanols contributes to photoprotection against UV-irradiation, increases dermal blood flow and skin thickness, improves skin density and moisture, and influences significantly the skin structure and roughness (Heinrich, U., et al., Long-term ingestion of high flavanol cocoa provides photoprorection against UV-induced erythema and improves skin condition in women. J. Nutr., 2006. 136: p. 1565-1569). In another study from the same group, an increase in dermal blood flow and oxygen saturation of haemoglobin was detected within two hours after ingestion of a single-dose of flavanol-rich cocoa (Neukam, K., et al., Consumption of flavanol-rich cocoa acutely increases microcirculation in human skin. Eur J Nutr, 2007. 46: p. 53-56).

Polyphenols are powerful natural anti-oxidant and anti-radical substances. Polyphenol extracts and preparations which contain them are usually used in the following indications: circulatory disorders, venous-lymphatic insufficiency, cutaneous capillary fragility, retinal circulatory disorders, haemorrhoids, rashes caused by the sun or associated with the effect of radiation (prevention of damage caused by radiotherapy), hypertension, hypercholesterolemia, various viral and microbial illnesses. Numerous publications have revealed types of action at a molecular level by which they are capable of fighting major illnesses including:

Cardiovascular Diseases:

Platelet antiaggregates (Petroni, A., M. Blasevich, M. Salami, N. Papini, G. F. Montedoro and C. Galli, "Inhibition of platelet aggregation and eicosanoid production by phenolic components of olive oil". Thromb Res, 1995. 78(2): p. 151-160)

Anti-inflammatories and protection against the oxidation of LDL-cholesterols (Frankel, E., J. Kanner, J. German, E. Parks and J. Kinsella, "Inhibition of oxidation of human low-density lipoprotein by phenolic substances in red wine". Lancet, 1993. 341(8843): p. 454-457).

Protection against the oxidation of eicosanoids (Pace-Asciak, C. R., S. Hahn, E. P. Diamandis, G. Soleas and D. M. Goldberg, "The red wine phenolics transresveratrol and quercetin block human platelet aggregation and eicosanoid synthesis: implications for protection against coronary heart disease". Clin Chim Acta, 1995. 235(2): p. 207-219)

Anti-atherosclerotics (Yamakoshi, J., S. Kataoka, T. Koga and T. Ariga, "Proanthocyanidin-rich extract from grape seeds attenuates the development of aortic atherosclerosis in cholesterol-fed rabbits". Atherosclerosis, 1999. 142(1): p. 139-149)

Anti-thrombotics (Fuhrman, B., A. Lavy and M. Aviram, "Consumption of red wine with meals reduces the susceptibility of human plasma and low-density lipoprotein to lipid peroxidation". Am J Clin Nutr, 1995. 61(3): p. 549-554)

Alzheimers (Orgogozo, J. M., J. F. Dartigues, S. Lafont, L. Letenneur, D. Commenges, R. Salamon, S. Renaud and M. Breteler, "Wine consumption and dementia in the elderly: A prospective community study in the Bordeaux area". Rev Neurol, 1997. 153(3): p. 185-192)

Cancer (Jang, M. S., E. N. Cai, G. O. Udeani, K. V. Slowing, C. F. Thomas, C. W. W. Beecher, H. H. S. Fong, N. R. Farnsworth, A. D. Kinghorn, R. G. Mehta, R. C. Moon and J. M. Pezzuto, "Cancer chemopreventive activity of resveratrol, a natural product derived from grapes". Science, 1997. 275 (5297): p. 218-220)

Taking into account the fact that cocoa contains polyphenols and of the importance of the use of polyphenols in the medical field, this has led to an attempt to extract the polyphenol compounds from cocoa, with the aim of creating dietetic food and drinks containing these antioxidants. The traditional pre-treatment, comprising fermentation followed by a drying operation, constitutes a major drawback in the sense that it reduces the levels of polyphenols contained in the resulting cocoa products.

US 2004/096566 discloses a process for carrying out the extraction under specific conditions that makes it possible to process cocoa beans to provide products with a high polyphenol content and enriched, (in comparison to the initial content of the beans) with certain useful lipid derivatives. The process disclosed in US 2004/096566 comprises the use of fresh beans, not having undergone a pre-treatment or defatting, these beans having had their pulp and shell removed, in such a way as to obtain clean kernels, the grinding of said kernels in the presence of a solvent, the maceration of the ground kernels under conditions allowing the desired compounds to be extracted, the filtration of the maceration mixture, and the recovery of the extract containing said compounds from the filtrate.

US 2007/0258920 discloses a further process for the production of cocoa based materials having enhanced levels of polyphenols.

WO2007/002883 discloses products, including beverages, that contain polyphenols and sterol and/or stanol esters, that are produced by a method which conserves the levels of polyphenols found in the starting materials. This document teaches that the acidification of polyphenol-containing ingredients helps to retain their levels of polyphenols during their incorporation into the final products. The disclosed method is based on combining all the ingredients of the product together and thereafter adding acid to reduce the pH before further processing.

However, problems relating to handling, stability and consumer appeal can occur with cocoa based beverages. These problems are particularly relevant in the case of beverages that contain cocoa based materials having an enhanced level of polyphenols. The present invention seeks to provide an improved process for preparing a beverage containing a cocoa based material having an enhanced level of polyphenols, and an improved beverage that contains a cocoa based material having an enhanced level of polyphenols.

According to the present invention there is provided a process for producing a beverage comprising a cocoa material having an enhanced level of polyphenols, the process comprising the steps of:

(a) adding a base to an aqueous phase to adjust the pH to between about 6.5 and about 7.5, (b) mixing ingredients into the aqueous phase to give a dispersion, the ingredients including the cocoa material having an enhanced level of polyphenols, (c) performing a thermal treatment on the dispersion, comprising heating the dispersion to over about 85° C. for at least about 5 seconds, and (d) cooling the treated dispersion.

Preferably, the aqueous phase is milk.

Conveniently, the milk is a low fat milk.

Advantageously, the aqueous phase is water.

Preferably, the base comprises potassium hydroxide, sodium hydroxide and/or potassium carbonate.

Conveniently, the pH of the aqueous phase in step (a) is adjusted to between about 6.7 and about 7.2.

Advantageously, the pH of the aqueous phase in step (a) is adjusted to between about 6.85 and about 7.1.

Preferably, the pH of the aqueous phase in step (a) is adjusted to between about 6.9 and about 7.0.

Conveniently, the cocoa material having an enhanced level of polyphenols is a cocoa powder.

Advantageously, the cocoa powder contains a higher level of polyphenols than alkalized cocoa powder.

Preferably, the cocoa powder has an ORAC value of greater than 1000 micromoles TE/g.

Conveniently, the cocoa powder has an ORAC value of greater than 1500 micromoles TE/g.

Advantageously, the cocoa powder contains at least 50 mg/g of polyphenols.

Preferably, the cocoa powder contains at least 80 mg/g of polyphenols.

Conveniently, the cocoa powder contains at least 100 mg/g of polyphenols.

Advantageously, the ingredients are selected from the group consisting of cocoa powder, polyphenol-enhanced cocoa powder, thickening agents, flavouring agents, sugar, sugar replacers, and mixtures thereof.

Preferably, the thermal treatment comprises heating the dispersion to above about 90° C.

Conveniently, the thermal treatment comprises heating the dispersion to between about 93° C. and 97° C.

Advantageously, the thermal treatment comprises heating the dispersion for at least 10 seconds.

Preferably, the thermal treatment comprises heating the dispersion for at least 20 seconds.

Conveniently, the thermal treatment comprises heating the dispersion for between about 25 and 50 seconds.

Advantageously, the thermal treatment is performed using a tubular heat exchanger and/or a plate heat exchanger.

Preferably, a UHT treatment is performed on the dispersion after the thermal treatment.

Conveniently, the process further comprises homogenizing the dispersion after step (b).

Advantageously, the homogenization is performed in two steps.

Preferably, the dispersion is cooled to a temperature of less than about 30° C. in step (d).

Conveniently, the dispersion is cooled to a temperature of between about 15 and about 25° C. in step (d).

Advantageously, the process further comprises packaging the beverage into a container.

According to another aspect of the invention, there is provided a beverage comprising:
 0.5 to 3% cocoa powder,
 0.5 to 3% polyphenol-enhanced cocoa powder,
 0.01 to 0.07% carrageenan,
 5 to 20% sugar, and
 milk to 100%,
wherein the beverage is substantially free of agglomerated protein.

According to a further aspect of the invention, there is provided the use of a beverage of the invention for the prevention or treatment of cardiovascular disease, poor cognitive performance, poor skin health, poor immune system performance, cancer, prostrate enlargement, obesity, and/or depression.

BRIEF DESCRIPTION OF THE FIGURES

The present invention will now be described, by way of example, with reference to the accompanying figures, in which.

DETAILED DESCRIPTION OF THE INVENTION

Figure 1:
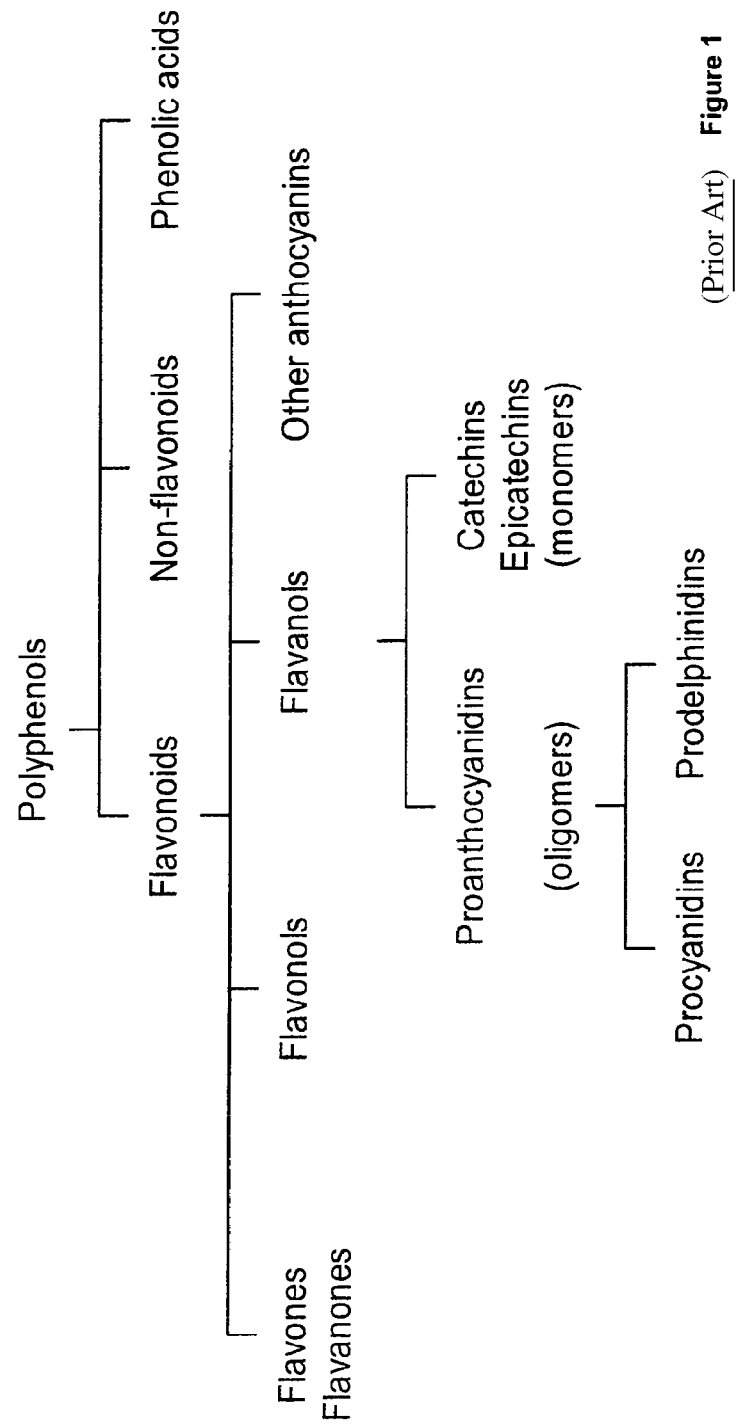
FIG. 1 is a schematic summary of the types of polyphenols that may be present in cocoa based material.
Figure 2:
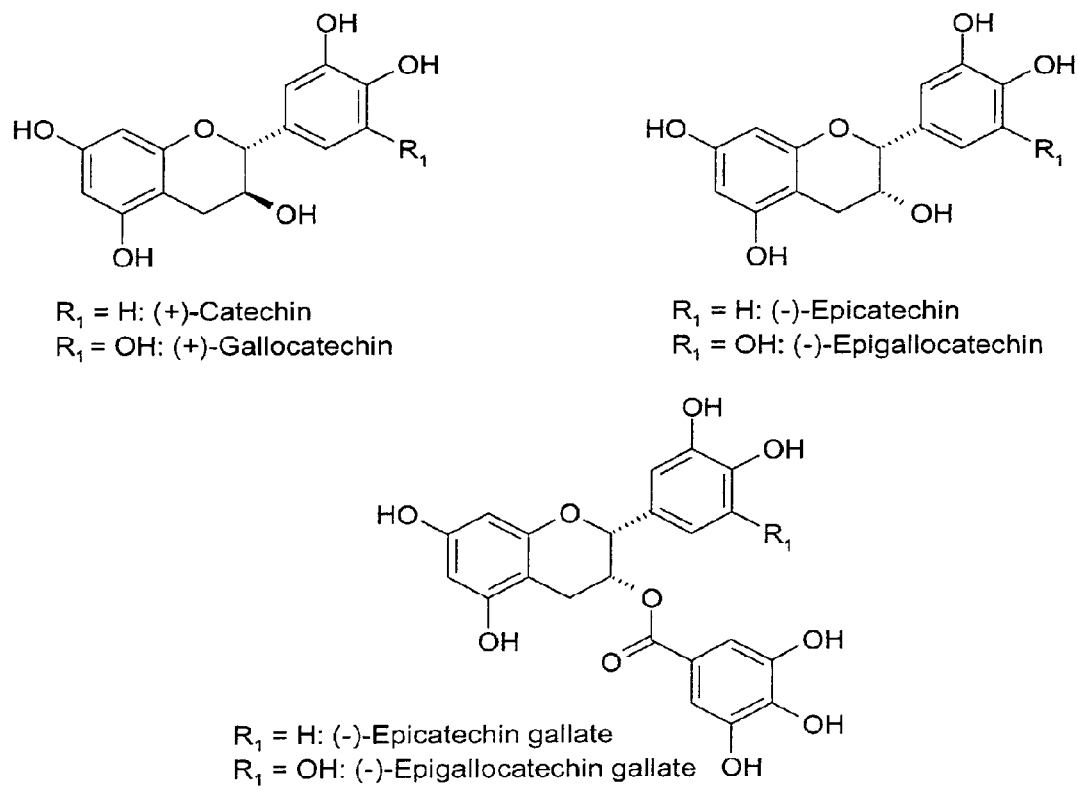
FIG. 2 shows the chemical structure of the cocoa polyphenols catechin, epicatechin and derivatives thereof.
Figure 3:
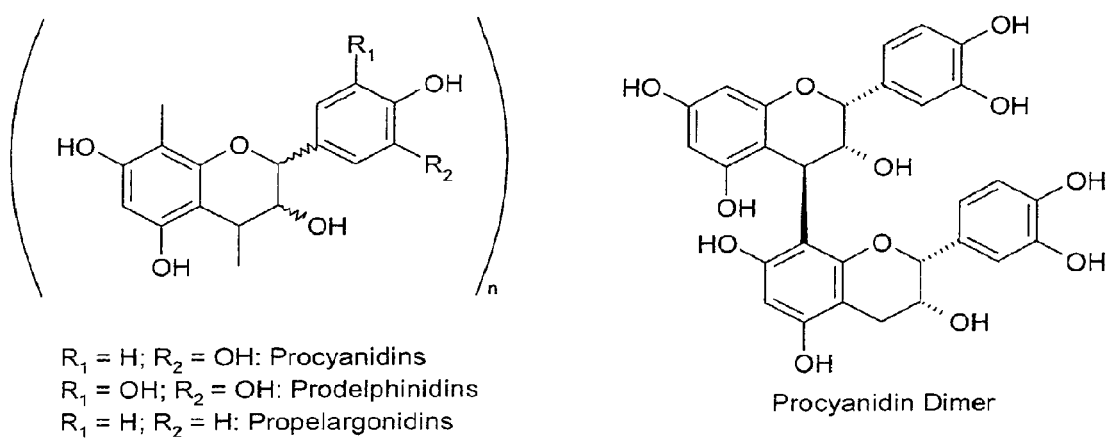
FIG. 3 shows the chemical structure of cocoa procyanidin polyphenols.

The listing or discussion of an apparently prior-published document in this specification should not necessarily be taken as an acknowledgement that the document is part of the state of the art or is common general knowledge.

Typically, the ingredients used in the beverages of the invention are selected from the group consisting of cocoa materials, sugars, sugar substitutes, milk powders, thickners, flavourings, emulsifiers and mixtures thereof. Preferably, the cocoa materials are selected from cocoa powder, cocoa mass, expeller flake, cocoa liquor, cocoa butter and mixtures thereof. Milk powders include, for example, skimmed milk powder, whey powder and derivatives thereof, full cream milk powder and mixtures thereof. Suitable sugars include sucrose, fructose, glucose and dextrose and mixtures thereof (of which sucrose is preferred). Sugar substitutes preferably include inulin, dextrin, isomaltulose, polydextrose and maltitol and mixtures thereof.

Sugar, may, for example, be glucose, fructose, lactose, or sucrose, or mixtures thereof; and is more preferably sucrose. Sugar replacers include, for example, mannitol, isomaltitol, xylitol, isomalt, lactitol, hydrogenated starch hydrolysates (HSH, including maltitol syrups), high fructose corn syrup and mixtures thereof. In one embodiment, the compositions are free of sugar replacers but comprise sugar, more preferably sucrose.

Thickeners include alginic acid, sodium alginate, potassium alginate, ammonium alginate, calcium alginate, propane-1,2-diol alginate, agar, carrageenan, processed eucheuma seaweed, locust bean gum (carob gum), guar gum, tragacanth, acacia gum, xanthan gum, karaya gum, tara gum, gellan gum, pectin, xanthan, starches and modified starches, and mixtures thereof. Preferred thickeners are carrageenan, xanthan, locust bean gum and mixtures thereof, with carrageenan being most preferred.

Beverages of the invention preferably comprise from 1 to 20% by weight of a sweetener selected from sucrose, sugar replacer and mixtures thereof, preferably from 3 to 15% by weight, more preferably from 5 to 10% by weight. The preferred sweetener is sucrose. Sugar replacers include, for example, mannitol, isomaltitol, xylitol, isomalt, lactitol, hydrogenated starch hydrolysates (HSH, including maltitol syrups) and mixtures thereof. In one embodiment, the beverages are free of sugar replacers but comprise sucrose.

Suitable emulsifiers include lecithin derived from soya bean, safflower, corn; fractionated lecithins enriched with either phosphatidyl choline, phosphatidyl ethanolamine, phosphatidyl inositol; emulsifiers derived from oats, mono- and diglycerides and their tartaric esters, monosodium phosphate derivatives of mono- and diglycerides of edible fats and oils, sorbitan monostearate, sorbitan tristearate, sucrose esters, polyoxyethylene sorbitan monostearate, hydroxylated lecithin, synthetic phospholipids such as ammonium phosphatides, lactylated fatty acid esters of glycerol and propylene glycol, polyglycerol esters of fatty acids, propylene glycol mono- and diesters of fats and fatty acids. It is preferred to use at least one of fractionated lecithin and polyglycerol polyricinoleate (PGPR) as the emulsifier.

Compositions of the invention will optionally comprise one or more flavourings. Suitable flavourings include, but are not limited to, fruit, nut, and vanilla flavourings, fruit powder and pieces, nuts, vanilla, herbs, herb flavourings, caramel and caramel flavourings. Vanillin is most preferred. Those skilled in the art are familiar with numerous flavourings than can be selected for use in this invention.

The compositions of the invention may optionally contain a preservative but are preferably free of added preservatives.

Preferably, the aqueous phase comprises a liquid selected from: water; milk (such as skimmed milk); soy milk; whey; oat milk; a solution, dispersion or suspension of milk solids (such as skimmed milk solids) in water; and mixtures thereof. Preferably the aqueous solution comprises sweetener and/or humectant, if present, and so may comprise sucrose, glucose syrup, fructose syrup or a mixture thereof.

A preferred homogenizer is a rotor/stator homogenizer. An example of a preferred rotor/stator homogenizer for use in the invention is that described in DE-A-4313149 (Imcatec GmbH; Lipp), the contents of which are incorporated herein by reference. The homogenizer is available commercially from Lipp Mischtechnik GmbH, Mannheim, Germany under the trade name Reflector®. The preferred rotor/stator homogenizer comprises a single-shaft inline mixer which works on the rotor/stator principle. Axially arranged rotor blades intermesh with the toothed rings of the stator. The toothed rings of the stator are preferably peripherally arranged. The toothed rings of the stator together with the ends of the rotors form a shearing zone. The homogenizer preferably comprises a hopper for adding the mixture and a conveying screw for delivering the mixture from the hopper to the rotor/stator elements. Other suitable homogenisers include a high shear Silverstone mixer and single stage or two stage homogenisers from Alfa Laval.

As mentioned above it is known that polyphenols can be beneficial to the health. There has been an interest in providing consumable products with enhanced levels of polyphenols. Cocoa is a natural product having high levels of polyphenols. There has been interest in improved methods of processing cocoa beans to retain high levels of polyphenols in the resultant products, including cocoa liquor, cocoa butter and cocoa solids such as cocoa powder.

One consumable product of interest is beverages or drinks that contain cocoa based material. However, the use of cocoa based materials having an enhanced level of polyphenols leads to problems such as the agglomeration and precipitation of proteins present in the drink. This can cause handling problems and can also be to reduce stability and consumer appeal. The present invention provides a process for the preparation of drinks that contain cocoa based materials, particularly cocoa based materials having an enhanced level of polyphenols, which addresses the problem of protein agglomeration. The forms 'drink' and 'beverage' as used herein are intended to have equivalent meanings.

The term "protein agglomeration", as used herein, is intended to mean the grouping together of protein molecules in a cocoa material containing drink which can lead to changes in the physical and optical properties of the drink, including precipitation of material. The agglomeration may be caused by at least partial denaturing of proteins and/or their association with other materials that may be present in the drink. The inventors have found that the use of cocoa based materials having an enhanced level of polyphenol may exacerbate these problems.

Without wishing to be bound by theory, the problem of protein agglomeration may be caused by the physical and chemical interaction between the polyphenol compounds from the cocoa based material, and protein molecules from the cocoa based material and other ingredients.

By "polyphenol" we mean the well-known group of chemical substances that are found in plants, characterised by the presence more than one phenol group per molecule. Polyphenols are often present as monomers, dimers, trimers and other oligomers. Flavonoids are a subset of polyphenol. Cocoa contains polyphenols such as catechin, epicatechin, gallocatechin, epigallocatechin, epicatechin gallate, epigallocatechin gallate, procyanidins, prodelphinidins, and propelargonidine. Preferred polyphenols include procyanidins A2, B1 to B5, and C-1. Polyphenols with a molecular weight of less than 3000 are preferred.

By "enhanced levels of polyphenols" it is meant that the cocoa based material contains a level of polyphenols that is higher than that found in traditionally prepared cocoa based materials. One example of traditionally prepared cocoa based material is alkalized cocoa powder. Thus, a cocoa powder that contains more polyphenols than an alkalized cocoa powder has an enhanced level of polyphenols. A cocoa powder that contains an enhanced level of polyphenols may be prepared using a controlled cocoa bean fermentation process. More specifically, a cocoa powder having an enhanced level of polyphenols contains at least 50 mg of polyphenols per gram of cocoa powder (50 mg/g). More preferably, a cocoa powder having an enhanced level of polyphenols has at least 60, more preferably at least 80 and most preferably at least 100 mg/g polyphenols.

An alkalised cocoa powder will generally contain no more than about 35 mg/g polyphenols. A natural cocoa powder will generally contain more polyphenols than an alkalised cocoa powder, with a maximum level of around 60 mg/g. However, natural cocoa powders have a relatively low pH of around 5.5 which can cause problems with protein agglomeration. Preferred cocoa based materials having enhanced levels of polyphenols are those with a pH greater than that of natural cocoa powder, more preferably having a pH of greater than about 6, most preferably having a pH of between about 6.2 and about 6.4.

Preferably, the drinks of the invention do not contain any added alcohol. Preferred drinks of the invention are substantially free from alcohol.

The cocoa based material used in the drinks has an enhanced level of polyphenols and is preferably derived from cocoa beans using a process designed to retain the polyphenols present in the harvested cocoa beans.

One well known way to determine the level of polyphenols in a product is to measure its ORAC value. ORAC stands for Oxygen Radical Absorbance Capacity and is a measurement for the capacity of a sample to neutralize free radicals. This capacity can be measured using a test method known as the ORAC assay.

This test uses AAPH as a physiological relevant radical generator and fluorescein as a fluorescent probe. As an internal standard in this assay, Trolox (a water-soluble analogue of vitamin E) is used. Fluorescein is an intense and long lasting-fluorescent probe. Reaction of AAPH with fluorescein leads to a loss of fluorescence. When a sample of material has antioxidative capacities, it neutralizes/scavenges the AAPH radicals and thereby protects the fluorescein from losing its fluorescence. This antioxidant capacity of a sample of material, as measured using the ORAC assay, is called the ORAC value. Since Trolox is used as an internal standard, this ORAC value is expressed as Trolox Equivalents or TE. The international standard way of expressing an ORAC value is micromol TE/mg (or mL) of sample. For particular applications, ORAC values may be converted to other units such as TE/Liter or TE/serving. As used herein, the ORAC value is a value indicating the antioxidant capacity of a sample of material as expressed in units of micromoles Trolox Equivalents (TE) per gram of material (micromoles TE/g).

Preferably, the cocoa based material having an enhanced level of polyphenols used in the present invention has an ORAC value of over 1,000 micromoles TE/g, more preferably above 1,500 micromoles TE/g.

One preferred cocoa based material having enhanced level of polyphenols is available from the Barry Callebaut group under the brand name ACTICOA™. A sample of ACTICOA™ cocoa powder has been measured to have an ORAC value of 2129 micromoles TE/g. This is higher than a measured ORAC value of natural cocoa powder of 826 micromoles TE/g, which itself is higher than the level for traditionally prepared alkalized cocoa powder, of which a sample had a measured ORAC value of 402 micromoles TE/g. Also, ACTICOA™ cocoa powder has a pH of around 6.3.

The inventors have found that careful control over the process for producing a beverage can reduce or eliminate problems relating to protein agglomeration. The process involves the provision of an aqueous phase an adjustment of the pH of the aqueous phase to between about pH 6.5 and 7.5 by the addition of a base. The base is preferably an alkali, and more preferably potassium hydroxide. The skilled person will realise that other edible bases and alkalis may be used. The aqueous phase may be, for example, water or milk. If milk is used, it is preferably a low fat milk.

After the pH of the aqueous phase has been adjusted by the addition of a base, the other ingredients of the beverage are added to the aqueous phase. The ingredients are mixed into the aqueous phase to give a dispersion. The ingredients include a cocoa based material which has an enhanced level of polyphenols. The cocoa material may be cocoa powder, cocoa mass, cocoa liquor, and cocoa butter. Preferably, the cocoa based material having enhanced levels of polyphenols is a cocoa powder, more preferably ACTICOA™ cocoa powder available from the Barry Callebaut group. The other ingredients added to the aqueous phase may include typical ingredients of cocoa based beverages, including cocoa materials, sugars, sugar substitutes, milk powders, thickeners, flavourings and emulsifiers.

Preferably, the ingredients include a cocoa based material other than and in addition to the cocoa based material which has enhanced levels of polyphenols. The ingredients also preferably include sucrose, milk powder, carrageenan as a thickener and lecithin as an emulsifier. The ingredients also preferably include vanillin as a flavouring agent.

These ingredients are mixed into the aqueous base to give a dispersion. Following the formation of the dispersion of the ingredients in the aqueous phase, the dispersion undergoes a thermal treatment. The thermal treatment comprises heating the dispersion to a temperature of over about 85° C. for at least 5 seconds. In other words, the dispersion is heated to and held at a temperature of over about 85° C. for a period of at least 5 seconds before cooling or being allowed to cool. In a preferred process, the thermal treatment involves heating the dispersion to around about 90° C. Preferably, the thermal treatment involves heating the dispersion to a temperature of no more than about 95° C.

Also, the thermal treatment preferably involves heating the dispersion to the required temperature for at least 10 seconds, more preferably at least 20 seconds and most preferably for between about 25 and about 50 seconds. The thermal treatment step may be carried out with equipment known in the art, such as tubular heat exchangers and/or plate heat exchangers.

Before the thermal treatment, the dispersion may undergo an optional homogenisation process. This may be performed using equipment and procedures known in the art, such as a two-stage homogenizer operating at 200 bar (180/20), and 65° C. A single stage homogenizer operating at from 125 to 220 bar could be used. These homogenizers operate by spraying liquid at high pressure onto a plate to disperse the fat particles and homogenise them in the liquid.

The dispersion may also undergo a UHT treatment in accordance with known procedures and practice. A preferred treatment is an indirect UHT method which involves heating the dispersion to between about 135° C. to about 142° C. for a length of time between about 2 and 10 seconds.

The beverage may also undergo a sterilisation process known in the art, which may involve heating glass containers of the beverage in a sterilisation tower at about 110° C. to 120° C. for about 20 to 30 seconds.

The heat treated dispersion is then cooled, either passively or actively, again using known equipment and procedures such as tubular heat exchangers or plate heat exchangers. The dispersion is preferably cooled to a temperature of less than 30° C., more preferably to a temperature of between about 15 and 25° C. After cooling, the dispersion may be packaged into suitable containers using known techniques, such as aseptic form-fill-seal procedures.

In a preferred embodiment, a beverage according to the invention comprises from 0.5 to 3% cocoa powder, from 0.5 to 3% polyphenol enhanced cocoa powder, from 0.01 to 0.07% carrageenan, from 5 to 25% sugar, and milk to 100%. Preferably, the beverage of the present invention is substantially free of agglomerated protein.

The beverages of the invention contained enhanced levels of polyphenols and so may have health benefits. In particular, the health benefits may include benefits relating to cardiovascular health, cognitive performance, skin health, immunity, cancer prevention, prostrate enlargement, weight management, anti-depression, anti-oxidant and anti-obesity.

The following non-limiting examples illustrate the invention and do not limit its scope in any way. In the examples and throughout this specification, all percentages, parts and ratios are by weight unless indicated otherwise.

It will be appreciated that the various percentage amounts of the different components that are present in the compositions of the invention, including any optional components, will add up to 100%.

EXAMPLES

Example 1

Production of a High Polyphenol Chocolate Beverage

1. Low fat milk (from 1,000 to 20,000 liters) is introduced into a tank. The temperature of the milk may be from 5° C. to 50° C., preferably about 10° C.
2. Potassium hydroxide is added to the tank via the supply funnel, and the milk is pumped in a circuit from the tank and back in via the supply funnel to mix in the alkali. The pH of the milk is monitored and more alkali is added until the desired pH of about 6.95 is reached (protein stabilising step).
3. Ingredients are then added via the supply funnel and circulated with the milk to result in a mixed dispersion. The added ingredients are set out below:
   1.25% DP10/12 cocoa powder (an alkalised cocoa powder with a fat content of between 10% and 12%)
   1.25% Acticoa™ cocoa powder
   0.03% carageenan
   0.01% vanillin
   9% sugar
   88.46% low fat milk
4. The dispersion is pumped over a two step homogeniser (Alfa Laval) at 200 bar (180/20) and 65° C.
5. The dispersion then undergoes a thermal treatment by being pumped through a tubular heat exchanger to bring the temperature of the dispersion to about 95° C. for about 30 seconds. A plate heat exchanger is also suitable for performing the thermal treatment step.
6. The thermally treated dispersion then undergoes a standard UHT treatment (heating to 137° C. for 5 seconds). This is an optional step.
7. The dispersion is then cooled to about 20° C. over a plate heat exchanger.
8. The resulting beverage is aseptically filled into 0.5 L PE bottles.

The invention claimed is:

1. Process for producing a beverage free of agglomerated protein comprising a cocoa powder containing at least 50 mg/g of polyphenols, the process comprising the steps of:
   (a) adding a base to milk to adjust the pH to between about 6.5 and about 7.5,
   (b) mixing ingredients into the milk to give a dispersion, the ingredients including the cocoa material having an enhanced level of polyphenols of at least 50 mg/g,
   (c) performing a thermal treatment on the dispersion, comprising heating the dispersion to over about 85° C. for at least about 5 seconds,
   (d) cooling the treated dispersion, and
   (e) obtaining a beverage free of agglomerated protein.

2. A process according to claim 1 wherein the milk is low fat milk.

3. A process according to claim 1 wherein the base comprises potassium hydroxide, sodium hydroxide and/or potassium carbonate.

4. A process according to claim 1 wherein the pH of the milk in step (a) is adjusted to between about 6.7 and about 7.2.

5. A process according to claim 1 wherein the pH of milk in step (a) is adjusted to between about 6.85 and about 7.1.

6. A process according to claim 1 wherein the pH of the milk in step (a) is adjusted to between about 6.9 and about 7.0.

7. A process according to claim 1 wherein the cocoa powder has an Oxygen Radical Absorbance Capacity ("ORAC") value of greater than 1000 micromoles TE/g, wherein "TE" is Trolox Equivalents.

8. A process according to claim 1 wherein the cocoa powder has an ORAC value of greater than 1500 micromoles TE/g.

9. A process according to claim 1 wherein the cocoa powder contains at least 80 mg/g of polyphenols.

10. A process according to claim 1 wherein the cocoa powder contains at least 100 mg/g of polyphenols.

11. A process according to claim 1 wherein the ingredients are selected from the group consisting of cocoa powder, polyphenol-enhanced cocoa powder, thickening agents, flavouring agents, sugar, sugar replacers, and mixtures thereof.

12. A process according to claim 1 wherein the thermal treatment comprises heating the dispersion to above about 90° C.

13. A process according to claim 1 wherein the thermal treatment comprises heating the dispersion to between about 93° C. and 97° C.

14. A process according to claim 1 wherein the thermal treatment comprises heating the dispersion for at least 10 seconds.

15. A process according to claim 1 wherein the thermal treatment comprises heating the dispersion for at least 20 seconds.

16. A process according to claim 1 wherein the thermal treatment comprises heating the dispersion for between about 25 and 50 seconds.

17. A process according to claim 1 wherein the thermal treatment is performed using a tubular heat exchanger and/or a plate heat exchanger.

18. A process according to claim 1 wherein an Ultra High Temperature (UHT) treatment is performed on the dispersion after the thermal treatment.

19. A process according to claim 1 further comprising homogenizing the dispersion after step (b).

20. A process according to claim 19 wherein the homogenization is performed in two steps.

21. A process according to claim 1 wherein the dispersion is cooled to a temperature of less than about 30° C. in step (d).

22. A process according to claim 1 wherein the dispersion is cooled to a temperature of between about 15° C. and about 25° C. in step (d).

23. A process according to claim 1 further comprising packaging the beverage into a container.

* * * * *